(12) United States Patent
Muller

(10) Patent No.: US 7,744,909 B2
(45) Date of Patent: *Jun. 29, 2010

(54) DISPERSIONS FOR THE FORMULATION OF SLIGHTLY OR POORLY SOLUBLE AGENTS

(75) Inventor: Rainer H. Muller, Berlin (DE)

(73) Assignee: Abbott GmbH & Co., KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/408,967

(22) Filed: Apr. 24, 2006

(65) Prior Publication Data

US 2006/0188534 A1 Aug. 24, 2006

Related U.S. Application Data

(63) Continuation of application No. 09/915,549, filed on Jul. 27, 2001, now Pat. No. 7,060,285.

(30) Foreign Application Priority Data

Jul. 28, 2000 (DE) ................................. 100 36 871

(51) Int. Cl.
*A61K 9/00* (2006.01)
(52) U.S. Cl. ...................................... 424/400
(58) Field of Classification Search ........................ None
See application file for complete search history.

(56) References Cited

U.S. PATENT DOCUMENTS

| 4,801,455 A | 1/1989 | List |
| 5,534,502 A | 7/1996 | Seki et al. |
| 5,616,330 A | 4/1997 | Kaufman et al. |
| 5,651,991 A | 7/1997 | Sugiyama et al. |

FOREIGN PATENT DOCUMENTS

| DE | 3623376 A1 | 1/1988 |
| DE | 4440337 A1 | 5/1996 |
| EP | 0 296 845 A1 | 12/1988 |

(Continued)

OTHER PUBLICATIONS

Kan et al., "Development of nonionic surfactant/phospholipid o/w emulsion as a paclitaxel delivery system", *Journal of Controlled Release*, 58:271-278 (1999).

(Continued)

*Primary Examiner*—Robert A Wax
*Assistant Examiner*—Bethany Barham
(74) *Attorney, Agent, or Firm*—Jeffrey S. Melcher; Manelli Denison & Selter PLLC

(57) ABSTRACT

The invention provides a dispersion having an oily phase, an aqueous phase, in the form of an oil-in-water emulsion or a water-in-oil emulsion, and at least one active ingredient that is only slightly or with difficulty soluble in the oily phase and the aqueous phase. The dispersion is free from toxicologically dangerous organic solvents. The dispersion contains the active ingredient dissolved in a quantity that is greater than the quantity which results additively from its maximum solubility in the oily and the aqueous phase of the emulsion prior to forming the emulsion.

68 Claims, 6 Drawing Sheets

Light microscopy graph of dispersion containing 5 mg/mL Amphotericin B from example 19.

FOREIGN PATENT DOCUMENTS

WO    9513066 A    5/1995

OTHER PUBLICATIONS

H.A. Liebermann et al. (Ed.), Pharmaceutical Dosage Forms: Disperse Systems (vol. 2), 1996, Marcel Dekker Inc., New York, Seiten 305 und 317.

K.J. Steffens et al., O/W emulsions as carriers for micronised drug particles, Manuf. Chem., 63, 23-26 (1992).

P.C. Schmidt et al., Development of a Suspension-Emulsion System for Parenteral Application in Animals, Acta Pharm. Technol., 35(1), 34-37 (1989).

Georg Achleitner, Eidesstattliche Versicherung.

J. Pasich, Emulgatory Z Grupy Trojterpenojdow, Farmacja Polska 21, 661-665 (1965).

J. Pasich, Emulgatoren aus der Gruppe der Triterpene Teil V, Pharmazie in Polen.

The Merck Index (1996), Seite 200, Monographle 1237 "Betulin".

M. Laszczyk, Triterpentrockenextrakt aus Birkenkork (Betula alba cortex) (2007), Auszug aus Dissertation: Zusammenfassung und Seiten 65, 67, 81 und 156.

K.J. Steffens et al., O/W Emulsions as Vehicles for Micronized Drug Particles, Eur. J. Pharm. Biopharm. 37(4), 219-226 (1991).

A.M. Kaukonen et al., Water-soluble B-cyclodextrins in paediatric oral solutions of spironolactone: solubilization and stability of spironolactone in solutions of B-cyclodextrin derivatives, International Journal of Pharmaceutics, 159, 159-170 (1997).

G.J. Vanderheiden et al., Construction of a Laboratory Press for Use with the French Pressure Cell, Applied Microbiology, 19(5), 875-8877 (1970).

S. Venkataram et al., Pharmacokinetics of Two Alternative Dosage Forms for Cyclosporine: Liposomes and Intralipid, Journal of Pharmaceutical Sciences, 79(3), 216-219 (1990).

V. Joly et al., Amphotericin B in a lipid emulsion for the treatment of cryptococcal meningitis in AIDS patients, Journal of Antimicrobial Chemotherapy, 38, 117-126 (1996).

V. Joly et al., In Vitro Renal Toxicity and In Vivo Therapeutic Efficacy in Experimental Murine Cryptococcosis of Amphotericin B (Fungizone) Associated with Intralipid, Antimicrobial Agents and Chemotherapy, 38(2), 177-183 (1994).

P. Chavanet et al., In-vivo activity and tolerance of conventional formulation versus fat emulsion formulation of amphotericin B in experimental disseminated candidiasis in neutropenic rabbits, Journal of Antimicrobial Chemotherapy, 39, 427-430 (1997).

D. Caillot et al., Efficacy and tolerance of an amphotericin B lipid (Intralipid) emulsion in the treatment of candidaemia in neutropenic patients, Journal of Antimicrobial Chemotherapy, 31, 161-169 (1993).

A.G. Floyd, Top ten considerations in the development of parenteral emulsions, Pharmaceutical Science & Technology Today (PSTT) 2(4), 134-143 (1999).

R. H. Muller et al., Emulsions and Nanosuspensions for the Formulation of Poorly Soluble Drugs, 1198, Medpharm Scientific Publishers, Stuttgart, Seiten 38, 177 and ruckseitiger Einband.

W.J. Lecluse, Preparation of Emulsions and Dispersions Using High-Pressure Homogenizers, International Symposium on Mixing (Feb. 21-24, 1978, Seiten XA-a bis XA-17.

Notice of Opposition and Opposition in Corresponding European Patent Application which explains relevance of documents cited in this Information Disclosure Statement.

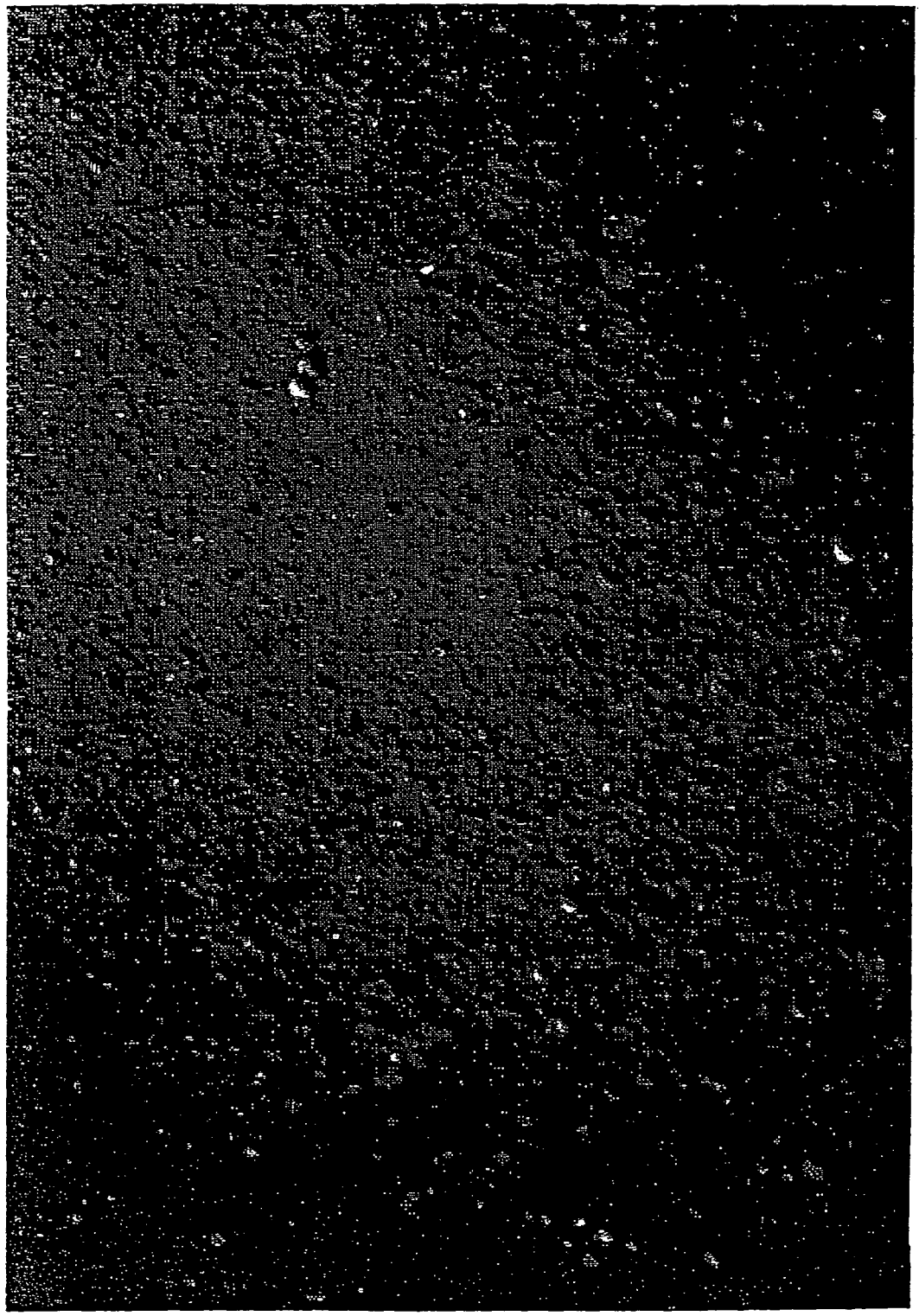
Fig. 4: Light microscopy graph of undiluted emulsion from example 18.

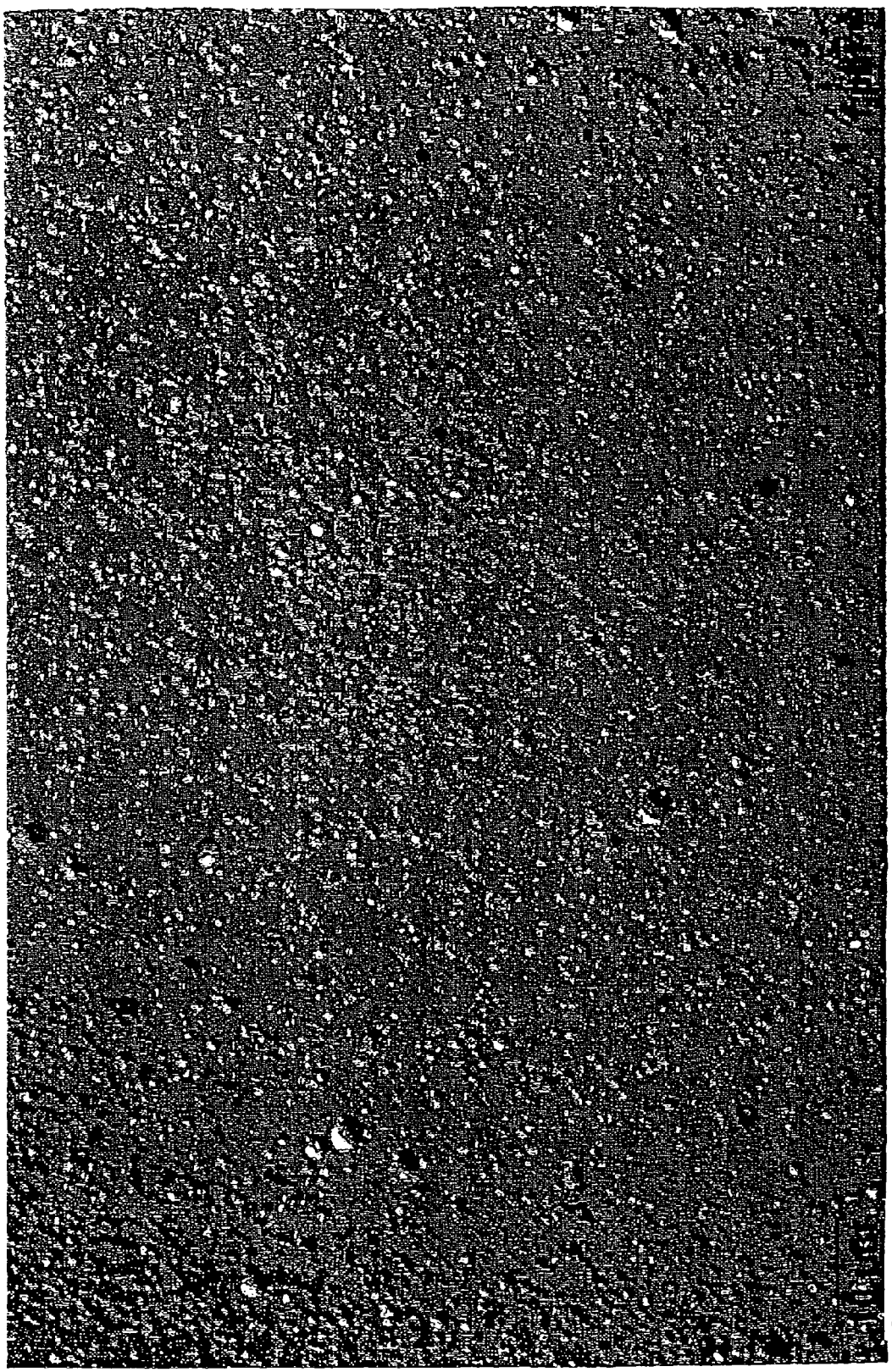
Fig. 5: Light microscopy graph of emulsion with 1mg/mL Amphotericin B from example 19.

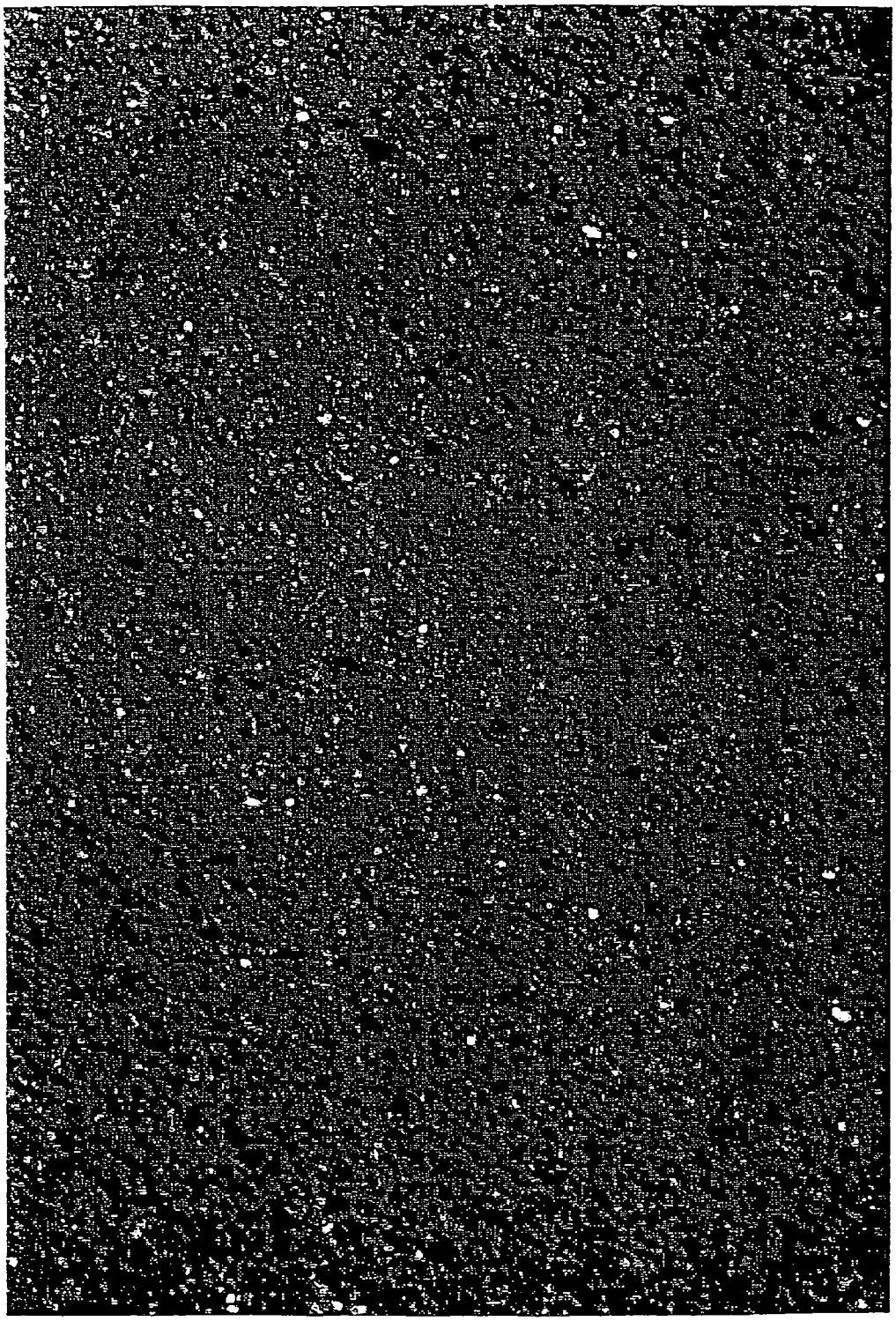
Fig. 6: Light microscopy graph of dispersion containing 5 mg/mL Amphotericin B from example 19.

DISPERSIONS FOR THE FORMULATION OF SLIGHTLY OR POORLY SOLUBLE AGENTS

This application is a continuation of U.S. application Ser. No. 09/915,549, filed Jul. 27, 2001, which claims priority to German Patent Application No. 10 36 871.9, filed on Jul. 28, 2000, the complete disclosure of which is incorporated herein by reference.

1. FIELD OF THE INVENTION

The invention relates to dispersions having an oily phase, an aqueous phase, and an active ingredient, which the active ingredient can only be dissolved slightly or is insoluble in both phases.

2. BACKGROUND OF THE INVENTION

Active ingredients with low solubility very often have the problem of insufficient bioavailabiliy. The solution generally adopted for this problem is increasing the solubility of these active ingredients. Examples of this are using a dissolving intermediary via solubilization, the formation of inclusion compounds (e.g. with cyclodextrines) and the use of solvent mixtures (K. H. Bauer, K.-H. Frömming, C. Führer, Pharmazeutische Technologie, Georg Thieme Verlag Stuttgart, 1991). For many active ingredients, however, this does not lead to a sufficient increase in solubility, especially if active ingredients are simultaneously difficult to dissolve in aqueous media and in organic media. Here, for example, solvent mixtures are ruled out as a solution to the problem. Alternatively active ingredients which are only slightly soluble in water can be dissolved in oils, an O/W emulsion can be produced and this can then be administered orally or parenterally, usually intravenously. Very many active ingredients, especially active ingredients which are at the same time only slightly soluble in aqueous and organic media, are however not sufficiently soluble in oils. Not sufficiently means that, because the solubility is too low, the volume of emulsion to be administered for the necessary dose is too large.

Active ingredients that are only slightly soluble in water and in oils, such as Amphotericin B, can however be incorporated into emulsions (Seki et al. U.S. Pat. No. 5,534,502). To achieve this, however, additional organic solvents must be used. These solvents must then be removed again in intermediate stages of the emulsion production or from the product (Davis, Wash., EP 0 296 845 A1) in which however a certain residual solvent content remains in the product. In addition, this production process takes a great deal of time, and is cost-intensive, so that practically no products based on this technology are represented on the market. An alternative method is the intercalation of such substances as Amphotericin B into the phospholipid double membrane of liposomes; a commercial product is for example AmBisome® (Janknegt et al., Liposomal and lipid formulations of amphotericin B., Clin. Pharmacokinet., 23,279-291 [1992]). A disadvantage of this, however, is the very expensive production process, which means that, as a rule, it is used only in emergencies, when another treatment does not achieve the aim, or only for patients who are financially in a position to pay for the treatment. Thus there is a clear need for an economical formulation, which is at the same time as simple as possible to produce, unlike liposomes is stable in storage, does not require lyophilization and does not contain residual solvents.

There is therefore need for a dispersion which contains an active ingredient, which hitherto could only be dissolved slightly, with difficulty or not at all, that is dissolved in a quantity hitherto not possible. There is also a need for a dispersion which avoids the disadvantages described above, such as the use of additional organic solvents hitherto necessary to form a formulation.

SUMMARY OF THE INVENTION

An object of the present invention is to form a dispersion based on an oil-in-water ("O/W") emulsion or a water-in-oil ("W/O") emulsion loaded with active ingredient, which can at the same time be dissolved in water and in oils only slightly, or with difficulty, or not at all.

Another objective of the invention is to form a dispersion which is free of toxicologically dangerous organic solvents and containing the active ingredient dissolved in a quantity that is higher than the quantity resulting additively from its maximum solubility in the water and the oil phase of the emulsion.

These objectives and other objectives are obtained by a dispersion which comprises:

an oily phase;

an aqueous phase, in the form of an oil-in-water emulsion or a water-in-oil emulsion; and at least one active ingredient that is only slightly or with difficulty soluble in the oily phase and the aqueous phase, wherein the dispersion is free from toxicologically dangerous organic solvents and contains the active ingredient dissolved in a quantity that is greater than the quantity which results additively from its maximum solubility in the oily and the aqueous phase of the emulsion.

The invention also provides a method for the production of a dispersion which comprises:

an oily phase;

an aqueous phase, in the form of an oil-in-water emulsion or a water-in-oil emulsion; and at least one active ingredient that is only slightly or with difficulty soluble in the oily phase and the aqueous phase, wherein the dispersion is free from toxicologically dangerous organic solvents and contains the active ingredient dissolved in a quantity that is greater than the quantity which results additively from its maximum solubility in the oily and the aqueous phase of the emulsion, wherein the method comprises;

combining the aqueous phase, oily phase, and active ingredient to form a pre-dispersion in which the active ingredient is not completely dissolved; and mixing the emulsion to form the dispersion.

Preferably, the quantity of active ingredient dissolved is greater than the additive quantity by a factor of 2, more preferably 5, still more preferably 10 or even greater. The "additive quantity" is determined by dissolving the maximum possible quantity of active ingredient in the separate oily and aqueous phases (dissolving conditions being otherwise identical) corresponding to the constituents in the dispersion (saturation concentration), no further additional organic solvents being used. The dispersion according to the invention contains, in addition to the additive quantity, a superadditive quantity of dissolved active ingredient.

An important characteristic according to the invention is that, with the same composition, high-energy homogenization is preferably carried out, compared with low-energy dispersion (shaking, or blade stirrer).

The production of the dispersion according to the invention is carried out in particular excluding toxicologically dangerous organic solvents such as e.g. methylene chloride and

Particle size distribution of the Amphotericin powder before incorporation into the dispersion (1A) and particle size analysis of the dispersion according to the invention following incorporation of the Amphotericin powder (1B, Example 1), the drug particles are no longer detectable (laser diffractometry).

Figure 3:
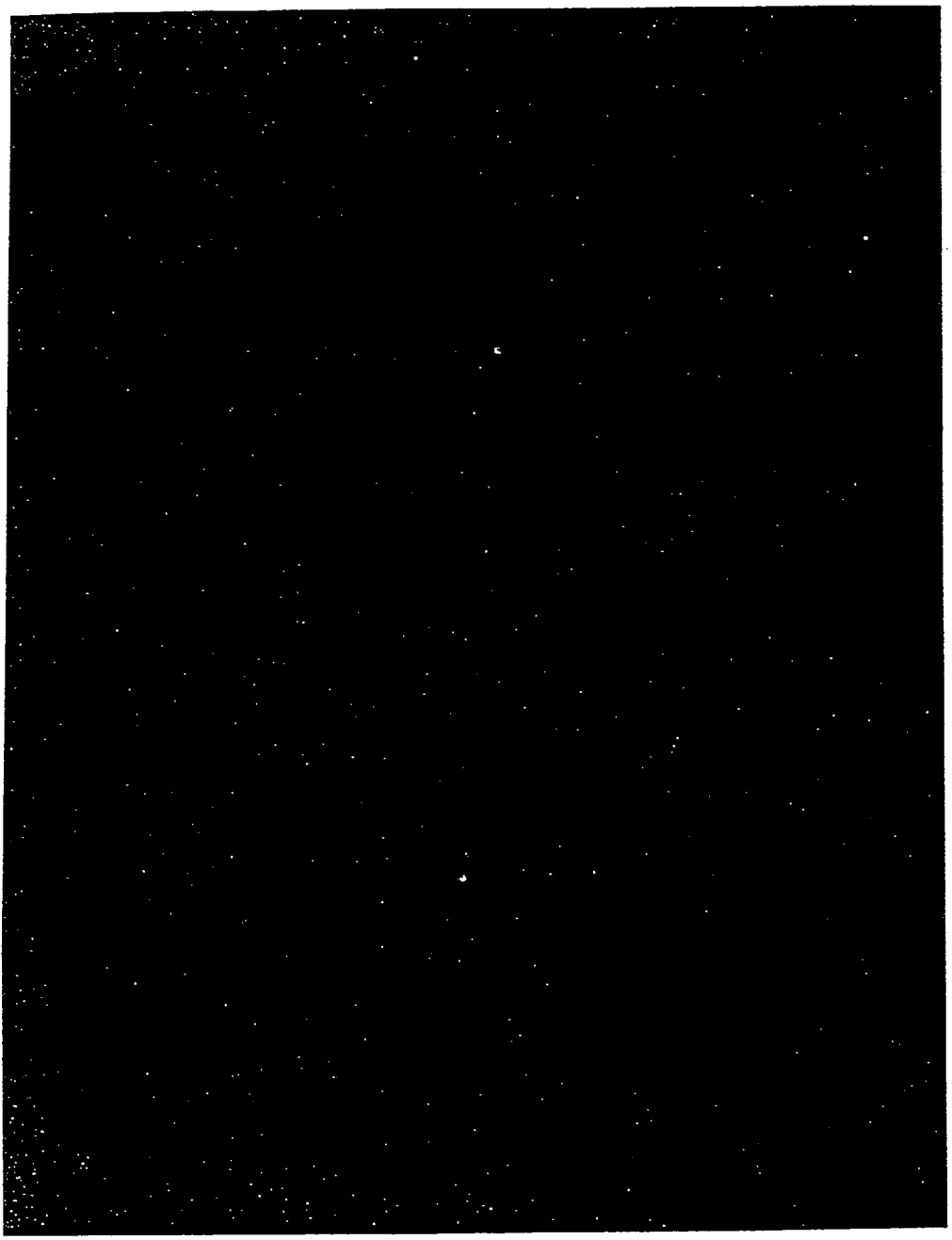

FIG. 2:

Light microscopic photograph of the Amphotericin powder before incorporation into the O/W emulsion (Example 1) (Polarization photograph in dark field, anisotropic crystals appear white, bar as in FIG. 3 (10 µm).

Figure 2:
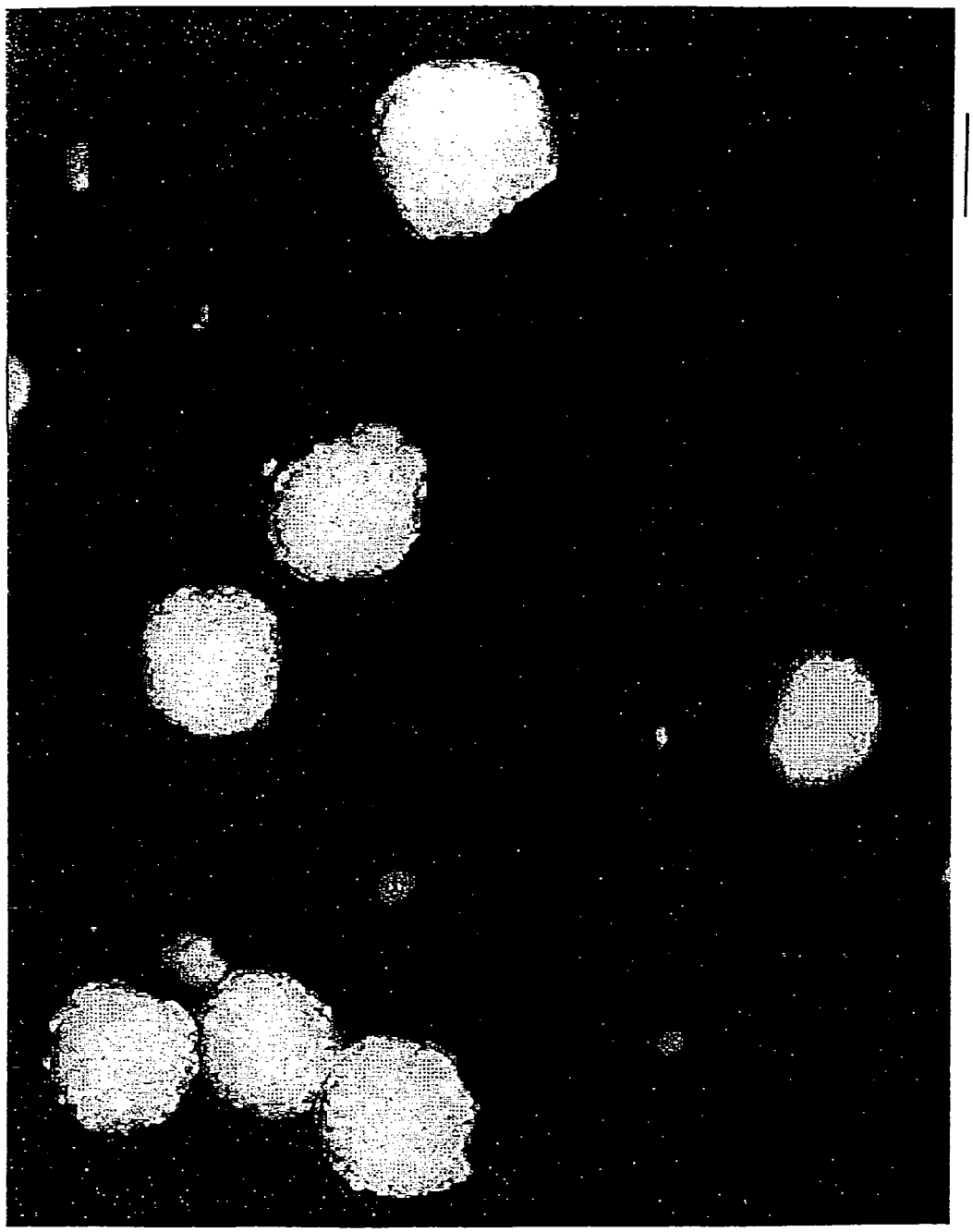

FIG. 3:

Light-microscopic photograph of the O/W emulsion after incorporation of the Amphotericin powder from FIG. 2 (Example 1) (polarization photograph, in dark field only diagrammatic reflexes of the isotropic emulsion drops, bar 10 µm).

FIG. 4:

Light microscopy graph of undiluted emulsion from example 18.

FIG. 5:

Light microscopy graph of emulsion with 1 mg/mL Amphotericin B from example 19.

FIG. 6:

Light microscopy graph of dispersion containing 5 mg/mL Amphotericin B from example 19.

DETAILED DESCRIPTION OF THE INVENTION

It is a generally recognized state of the art, that the molecules of an active ingredient that can be dissolved only with difficulty or slightly, must be incorporated from the solid aggregate condition (powder) via at least one intermediate step (e.g. molecular dispersive distribution in a solvent) into an emulsion as a carrier system. Experience shows that in the case of substances that are only very slightly soluble in water and oil at the same time, it is not sufficient to add crystals of the active ingredient to the emulsion. Thus the admixture of Amphotericin B-solution (solvent mixture), sometimes made to a commercial O/W emulsion such as Intralipid or Lipofundin, leads to the precipitation of the active ingredient, Amphotericin B crystals are produced, which sediment and do not dissolve in the emulsion.

Surprisingly, it has now been found that the production of an emulsion system with dissolved active ingredient is also possible direct from the solid aggregate condition of the active ingredient. To produce the dispersion according to the invention, the active ingredient is added to the aqueous phase or the oil phase in particle form and then all components are subjected to a fairly high- or high-energy process such as, for example, homogenization, especially high pressure homogenization. The high-energy process of high pressure homogenization leads to incorporation of the active ingredient into the emulsion by molecular dispersion, and no active ingredient crystals remain detectable in the polarization microscope. The emulsions obtained surprisingly have a stability similar to that of systems produced using organic solvents.

A very simple way of incorporating the active ingredient crystals is trituration of the active ingredient with a commercial O/W emulsion (e.g. Lipofundin, Intralipid). After trituration, the active ingredient is found primarily in the water phase, a disperse system has been produced, which, as an internal phase, simultaneously contains drops of oil and active ingredient crystals. This disperse system is then subjected to homogenization or high pressure homogenization (e.g. 1,500 bar and 5-20 homogenization cycles). A finely dispersed emulsion is obtained (Example 1) in which, at the end of the homogenization process no active ingredient crystals remain detectable. The crystals have almost completely or completely dissolved, i.e. using a light microscope, even with 1000-fold magnification, in 2 out of 3 fields, no more than 10 crystals, preferably no more than 5 crystals and especially no more than 1 crystal can be detected.

If desired, the active ingredient can, however, also be used in a quantity such that, at the end of the homogenization process, in addition to the dissolved part of the active ingredient, a part of the active ingredient in undissolved crystalline form is still present, which forms a depot.

Alternatively an aqueous suspension of the active ingredient can be mixed with an O/W emulsion. Again it is a disperse system with a dispersed phase of drops of oil and crystals of active ingredient. This is likewise subjected to a fairly high-, or high-energy process such as high pressure homogenization. Admixture of the active ingredient as an aqueous suspension is especially suitable if the active ingredient concentration is relatively low. In addition the aqueous suspension of the active ingredient can be subjected to a grinding process described in the textbooks before the admixture, e.g. wet grinding with a colloid mill, a pearl mill or a bead mill, or pre-pulverized by high pressure homogenization.

In general it is favorable to use the active ingredients in the form of very fine crystals, i.e. in micronized form with a particle size ranging from ca. 0.1 µm to 25 µm (colloid mill, gas-jet mill).

Alternatively the active ingredient can also be dispersed in the oil. The oil with the active ingredient crystals is then dispersed in the water phase, during which the necessary surfactant is either added to the water phase or dissolved in the oil phase or dispersed in each case. In the case of lecithin, the lecithin can be dispersed in the water or dissolved in the oil phase whilst being slightly heated.

In the case of incorporation of the active ingredient crystals into the oil phase, this can take place without the addition of a surfactant. The surfactant, e.g. lecithin, is then added. Alternatively the active ingredient crystals can also be incorporated into an oil phase, which already contains surfactant.

After incorporation of the active ingredient crystals into the oil, the oil phase is dispersed in water (e.g. with a high-speed agitator) and the raw emulsion obtained is then subjected to high pressure homogenization. Here too it is favorable to use the active ingredient crystals as small as possible. For the further comminution of the active ingredient crystals incorporated into the oil phase, this oily suspension, before producing the raw emulsion, can first be subjected to grinding. The active ingredient crystals in the oil phase are further comminuted by this wet grinding, partially into the nanometer range. Usual wet grinding processes which can be used are, for example, the colloid mill and high pressure homogenization of the oil phase. In general the cavitation of an aqueous phase is the recognized principle of comminution in the case of high pressure homogenization, i.e the presence of water is necessary for the cavitation. Oils with an extremely low vapor pressure compared to water cannot be used for cavitation. In spite of this it was surprisingly found that sufficient comminution occurs for the production of the new carrier system.

It is characteristic of the dispersion according to the invention, that the active ingredient incorporated in the emulsion is present dissolved in a higher quantity than that resulting additively from its maximum solubility in the water and oil phase of the emulsion, and at the same time no toxicologically dangerous organic solvents were used for production. Such toxicologically dangerous organic solvents include in particular chloroform, methylene chloride, fairly long-chained alcohols such as hexanol and octanol, but also ethanol in fairly high concentrations.

As a rule, the active ingredients according to the invention are active ingredients that are only slightly soluble (1 part dissolves in 30-100 parts solvent) or difficult to dissolve (1 part dissolves in 100-1000 parts solvent), but especially very difficult to dissolve (1 part dissolves in 1,000 to 10,000 parts solvent) or even insoluble (>10,000 parts solvent).

Thus the solubility of Amphotericin B in water is less than 0.001% (<0.01 mg/ml) at pH 6-7, i.e. the pH value of the emulsion. It is true that the solubility of Amphotericin is higher with pH 2 and pH 11 (0.1 mg/ml), however these solutions cannot be administered intravenously.

The solubility of Amphotericin in soya oil (Long-chain Triglycerides—LCT) and in Miglyol 812 (Medium-chain Triglycerides—MCT), the standard oils for most commercially available emulsions for parenteral infusion is less than 0.0001 mg/ml.

40 g emulsion from Example 1 consist 20% of oil (8 g) and ca. 80% of water (32 g). Thus on the basis of these solubilities, 8×0.0001 mg/ml plus 32×0.01 mg/ml, i.e. in total 0.3208 mg Amphotericin can be dissolved in 40 g emulsion components oil and water (i.e. approx. 0.008 mg/ml emulsion). In the present emulsion according to the invention 0.2 mg/ml emulsion could be incorporated (Example 1) without microscopic crystals of undissolved drug being detectable (Example 12). A higher concentration than 1 mg/ml emulsion could also be incorporated (Example 2), with laser diffractometry none of the drug particles used for production remained detectable (Example 11).

In the case of a desired dose of e.g. 100 mg Amphotericin B, the dispersions according to the invention with 1 or 0.2 mg/ml emulsion, result in a volume of 100 to 500 ml emulsion to be administered intravenously. Thus with the emulsion according to the invention, active ingredients which dissolve only slightly, or are difficult to dissolve, can for the first time be administered in a sufficiently small administration volume with well-tolerated pH values.

Dissolved active ingredient is rapidly available. For production of a depot preparation, more active ingredient can be incorporated into the dispersion than will dissolve in it, i.e. crystals are produced which act as a depot. The solubility in water and oil phase amounts to, for example, 0.008 mg/ml in the case of Amphotericin B, the emulsion according to the invention dissolves without detectable crystals e.g. 0.2 mg/ml (Example 1). If 5 mg/ml dispersion is incorporated, the solubility is exceeded (supersaturated system). Following high pressure homogenization, in addition to the dissolved active ingredient, very fine drug crystals are obtained (Example 15).

The heterogeneous, supersaturated dispersions produced by mixture of a drug (Example 15) or drug suspension (analogous to Example 6) with an emulsion are characterized in that small drops of oil and very fine crystals exist separately side by side, i.e. the crystals are primarily outside the oil drops.

Determination of the particle size is carried out by light microscopy, whilst establishing the number distribution. Alternatively this can be determined by laser diffractometry (Equipment: Coulter LS 230, Coulter Electronics, Krefeld, Germany), the volume distribution obtained can be converted into the number distribution.

If, in the dispersion with a high load of active ingredient, further drug crystals are present beside the emulsion droplets, directly after production at least 90%, and preferably 95% of the number of active ingredient crystals in the number distribution are smaller than 5 µm. With the application of high pressures (e.g. 1000 bar) and a sufficient number of homogenization cycles, highly disperse systems are obtained. Depending on pressure and number of cycles, dispersions are obtained with at least 90%, in some cases 95% and especially 99% of the number of crystals in the number distribution smaller than 1 µm.

A description is given above, of the in situ production of the active ingredient depot from small crystals, by production of the dispersion according to the invention with an active ingredient quantity above the saturation solubility of the system. Alternatively a dispersion according to the invention can also be produced with exclusively dissolved active ingredient, to which active ingredients of definite size are subsequently admixed, e.g micronized active ingredient.

To produce the dispersion according to the invention, commercial O/W emulsions can be used (e.g. Lipofundin, Intralipid, Lipovenoes, Abbolipid, Deltalipid and Salvilipid), or an emulsion is produced from oil phase, emulsifier/stabilizer and outer phase (e.g. water).

Examples of constituents of the oil phase of the emulsions are: soya oil, safflower oil (thistle oil), long-chain triglycerides (LCT), medium-chain triglycerides (MCT) such as, for example, miglyols, fish oils and oils with an increased constituent of unsaturated fatty acids, acetylated partial glycerides such as in Stesolid, individually or in mixtures.

For stabilization of the dispersions, emulsifiers and stabilizers can be used. These are possibly already contained in the emulsion used to produce the dispersion according to the invention, addition of further emulsifiers and stabilizers can be advantageous in the production of the dispersion.

Examples of emulsifiers are e.g. egg-lecithin, soya lecithin, phospholipids of egg or soya, Tween 80, sodium glycocholate and sodium lauryl sulphate (SDS). Alternatively stabilization can be carried out by the addition of substances which have the effect of increasing stability by mechanisms other than emulsifiers, e.g. by steric stabilization or increase of the zeta potential. Such stabilizers are e.g. block co-polymers such as e.g. poloxamers (e.g. Poloxamer 188 and 407) and poloxamines (e.g. Poloxamine 908), polyvinyl pyrrolidon (PVP), polyvinyl alcohol (PVA), gelatine, polysaccharides such as hyaluronic acid and chitosan and their derivatives, polyacrylic acid and its derivatives, polycarbophil, cellulose derivatives (e.g. methyl-, hydroxypropyl- and carboxymethyl cellulose), sugar esters such as saccharose monostearate and antiflocculants such as sodium citrate. Emulsifiers and stabilizers can be used individually or in mixtures. Typical concentrations are 0.1% to 20%, especially 0.5% to 10%. All amounts used herein are wt. %, based on the total weight of the dispersion, unless otherwise stated.

As an aqueous outer phase of the O/W emulsion used for production of the dispersion according to the invention the following can be used: water, mixtures of water with other water-miscible organic liquids, liquid polyethylene glycols (PEG, especially PEG 400 and 600).

The aqueous outer phase can also contain additives, e.g. electrolytes, non-electrolytes (e.g. glycerol, glucose, mannitol, xylite, for isotonization), gel forming agents such as cellulose derivatives and polysaccharides such as xanthane and alginate (e.g. to increase viscosity).

For topical application, penetration enhancers (e.g. azone, lauric acid) can be added to the dispersion and for application to the gastrointestinal tract, absorption enhancers (e.g. bile acids, lysophospholipids) can be added.

Active ingredients for incorporation into the emulsion are, besides Amphotericin B, e.g. Ciclosporin, Buparvaquone and Atovaquone. Further active ingredients are hormones (e.g. estradiol), antioestrogens and corticoids (e.g. Prednicarbate).

Administration of the emulsion can be carried out using different routes, e.g. parenterally, but also orally or topically. In the case of parenteral administration, all the usual methods are possible, e.g. intra- and subcutaneous, intramuscular, intra-articular, intraperitoneal etc.

Topical emulsions with Cyclosporin can improve the penetration of the active ingredient into the skin because of the high constituent of the drug dissolved (increased concentration gradient). Oral administration of the Cyclosporin emulsion can increase the bioavailability as, in contrast to micronized Cyclosporin, an increased dissolved constituent is present.

The bioavailability of orally administrated Amphotericin B is almost zero due to its low solubility. Oral administration of the Amphotericin emulsion can also increase the bioavailability due to the increased dissolved constituent.

The emulsions according to the invention (e.g. with Buparvaquone and Atovaquone) can, following intravenous injection, also be used for tissue-specific drug administration, by combination with a targeting unit (e.g. Apolipoprotein E in combination with Apolipoprotein AI and AIV) (targeting to the brain). In certain diseases of the monocyte/phagocyte system (MPS) exciters also become localized in the brain and hitherto have been difficult to access for therapy (e.g. Leishmanioses, Toxoplasmosis).

The systems described above are of O/W type, that means oil droplets are dispersed in the water phase. It is also possible to produce W/O emulsion based dispersions. A basic advantage is that the outer oil phase acts as a diffusion barrier prolonging drug release. Such dispersions cannot be administered intravenously, but they can e.g. be injected intramuscularly or subcutaneously as depot formulation. Application of W/O systems to the eye increases the retention time in the eye due to the increased viscosity and simultaneously provides prolonged drug release. For topical application to the skin, the oil phase has an occlusive effect increasing drug penetration. From this, the W/O type systems have advantages for special applications. Preferred form of the invention is however the O/W type dispersion.

For oil-in-water emulsions the dispersion is characterized in that it contains 5 to 99.5% by weight of aqueous phase, preferably 10 to 95% by weight of aqueous phase, more preferred 60 to 95% by weight and specifically 70 to 95% by weight of aqueous phase, based on the weight of the total dispersion.

For water-in-oil emulsions the dispersion is characterized in that it contains 5 to 30% by weight of aqueous phase, preferably 10 to 25% by weight of aqueous phase, more preferred 10 to 20% by weight of aqueous phase, based on the weight of the total dispersion.

The ingredients of the oil phase of the emulsions are—as mentioned above—in particular selected from the group consisting of soya oil, safflower oil, long-chain triglycerides (LCT), medium-chain triglycerides (MCT), such as miglyols, fish oils and oils with an increased amount of constituent of unsaturated fatty acids, acetylated partial glycerides, such as in Stesolid®, individually or in mixtures. The medium-chain triglycerides contain preferably at least 90% triglycerides of caprylic acid (C8) and of capric acid (C10). According to the invention mixtures of soya oil and MCT are suitable as oil phase, in particular in a weight ratio of 5:1 to 1:5, preferably 2:1 to 1:2 or 1:1.

The oil phase of the invented dispersions can consist of oils, that means lipids being liquid at room temperature of 20° C. It is also possible to blend these oils with lipids being solid at room temperature of 20° C. The blending mixture of oil and solid lipid can range from 99+1 to 1+99. Preferred blending mixtures contain a minimum of 10 parts liquid oil, especially 30 parts liquid oil and most favorable at least 50 parts liquid oil.

In special cases the lipid phase of the dispersion can consist 100% of lipid being solid at room temperature of 20° C. In case of lipids melting close to room temperature, this leads to dispersions of lipid droplets being in a super-cooled melt state. In case of very high melting lipids—despite the melting point depression according to the Thomson equation—the particles of the dispersion can harden. The Thomson equation describes that the melting point of lipids is strongly depressed compared to the bulk ware in case they crystalline as very fine particles (i.e. nanoparticles or having a size of a few micrometer) (Hunter, R. J., Foundations of colloid science, Vol. 1, Oxford University Press, Oxford, 1986).

Examples for lipids being solid at room temperature are carnauba wax, hydroxyoctacosanyl hydroxystearate, Chinese wax, cetyl palmitate, beeswax and similar waxes. Further examples of these solid substances include $C_{20-40}$ di- and triglycerides, including those which contain unsaturated fatty acids, $C_{20-40}$ fatty alcohols, $C_{20-40}$ fatty amines and their compounds, sterols.

Suitable lipids for the production of blends from liquid and solid lipids are: Natural and synthetic triglycerides and mixtures thereof, monoglycerides and diglycerides, alone or mixtures thereof or mixtures with e.g. triglycerides, self-emulsifying modified lipids, natural and synthetic waxes, fatty alcohols including their esters and ethers and mixtures thereof. Especially suited are synthetic monoglycerides, diglycerides and triglycerides as individual substances or mixtures thereof (e.g. hard fat), Imwitor 900, triglycerides (e.g. glyceroltrilaurate, glyceroltrimyristate, glyceroltripalmitate, glyceroltristearate and glyceroltribehenate) and waxes as e.g. cetylpalmitate, carnauba wax and white wax (German pharmacopeia). In addition paraffins, e.g. solid paraffin.

The droplet size of the oil droplets (O/W type) or water droplets (W/O type) in the dispersion is above 100 nm (determined by photon correlation spectroscopy—PCS). The recommended upper size limit is 10 µm, otherwise creaming will occur due to flotation of the droplets leading to physical instability (droplet coalescence). To minimize flotation, the size should be below 5 µm, preferentially below 1 µm (PCS diameter) leading to so-called physically "autostable" dispersions. Optimum physical stability was found in the size range similar to parenteral fat emulsions with PCS diameters of 200 nm to 500 nm.

The stabilizer content in parenteral preparations should be kept as low as possible to minimize toxicity and distortions of metabolism. From lecithin-containing emulsions for parenteral nutrition it is known, that a too high administration of lecithin can cause metabolic distortions, typical daily volumes administered are e.g. 500 ml emulsion and more. This lead to the development of lecithin-reduced emulsions, that means going even further down from 1.2% lecithin to 0.6% lecithin. Some systems for the delivery of poorly soluble drugs use a relatively high emulsifier content (e.g. solubilization with su rfactants, SE DDS—self-emulsifying drug delivery systems based on the solubilization of oil by high surfactant concentrations). A special feature of the present invention is that it minimizes the surfactant load.

A typical composition of OIW type of the invented dispersions is: 20 g oil, 1.2 g lecithin, 0.1 g drug and 78.3 g water. That means the 21.2 g produced oil droplets consisted of 20 g oil phase (=94.3%) and 1.2 g stabilizer (=5.7%).

Further examples of emulsifiers are in addition to lecithines the polyethoxysorbitanesters (Tween®-types), such as e.g. laurate (Tween 20/21), palmitate (Tween 40), stearate (Tween 60/61), tristearate (Tween 65), oleate (Tween 80/81), or trioleate (Tween 85) esters, sodium glycocholate and sodium laurylsulfate (SDS) as well as the sorbitan fatty acid esters (Spane-types).

In addition and preferably also surfactants, emulsifiers and stabilizers are used, which are admitted for use in and on humans (e.g. auxiliary agents having GRAS-status).

Especially for the W/O type dispersions, typical water-in-oil surfactants are used for stabilization, sometimes in mixtures, also with O/W emulsifiers. Examples are the fatty alcohols, ethylenglycolmonostearate, glycerolmonostearate, sorbitan fatty acid esters (Span® series, e.g. the Span 20, Span 40, Span 60 and Span 80 series, especially Span 85), ethers of fatty alcohols with polyethylenglycol (PEG) (e.g. Brij® series), esters of fatty acids with PEG (e.g. Myrj® series).

Again, in general surfactants and stabilizers are preferred having an accepted status, e.g. GRAS substances (Generally Regarded As Safe—Food Additives—GRAS substances, Food Drug Cosmetic Law Reports, Chicago (1994), Food Additive Database der FDA, Internet: www.fda.gov, 1999).

In case the dispersions according to the invention contain—additionally to the oil droplets—particles of non-dissolved active ingredient, the particle size should be as small as possible, e.g. to maintain physical stability and avoiding sedimentation. In addition, in case of intravenous administration the particles need to be small enough to avoid capillary blockade. The smallest capillaries being approximately 5-6 µm in diameter. Therefore the particle diameter 90% should be below 5 µm, preferentially also the diameter 95% and most preferentially the diameter 100% should be below 5 µm (measured by laser diffractometry after separation of the particles from the dispersion by centrifugation, volume distribution data). It is even more beneficial that these diameters are below 3 µm providing a certain safety distance to the smallest capillaries. Most advantageous is a particle size of non-dissolved drug below 1000 nm (mean particle size measured by photon correlation spectroscopy). This size is far away from the 5-6 µm smallest capillary diameter and simultaneously excludes any sedimentation effects (this size of particles does not sediment rather independent on the density of the drug). In case a more rapid dissolution of the drug crystals after administration of the dispersion is required, the mean PCS diameter should be in the range of 100 nm to approx. 400 nm, most favorable below 100 nm.

Generally it is advantageous, to use the active ingredient in form of very fine crystals for the production of the dispersions, i.e. in micronized form having a particle size in the range of about 0.1 µm-25 µm (colloid mill, gas-jet mill). Preferred are average particle sizes of 0.1 µm-5 µm, more preferred smaller than 1 µm.

The pH of the dispersions according to the invention is typically between 4 and 8, preferably between 5 and 7.5, more preferred between 6 and 7.5 and is determined in practice by way of the form or manner of application.

The dispersion according to the invention may further contain an effective amount of an antioxidant, such as vitamin E, in particular the isomer alpha-tocopherol. Alternatively, also beta- or gamma-tocopherol, or ascorbyl palmitate may be used. The amount added may be 10 mg to 2000 mg, preferably 25 mg to 1000 mg, based on 100 g of triglyceride.

A typical dispersion according to the invention thus can comprise, based on the ready-for-use-composition: 0.05 to 1.0 wt. %, preferably 0.05 to 0.5 wt. % of active ingredient, 0.05 to 2 wt. % of emulsifier or a mixture of emulsifiers, e.g. Tween 80 and/or egg-lecithin, dispersed in a O/W emulsion, which, based on the emulsion, contains 5 to 30 wt. %, preferably 10 to 20 wt. % triglycerides. The triglycerides are preferably soya bean oil, medium-chain triglycerides (at least 90% C8/C10) as well as mixtures of soya bean oil and medium-chain triglycerides (at least 90% C8/C10) in a weight ratio of 1:2 to 2:1, preferably 1:1. In addition also 0.5 to 5 wt. %, preferably 1 to 3 wt. % of typically used isotonisation agent, such as glycerol, and 0.005 to 0.05 wt. % antioxidants, such as alpha-tocopherol, may be present, based on the total composition. A particularly preferred active ingredient is amphotericin B. Further, also preservation agent may be added. This is in particular useful for packaging of the dispersions in multidispense-containers.

The dispersions contains the active ingredient dissolved in an amount, which is greater than that amount which is the result of the mathematical addition of its maximal solubility in each of the water phase and the oil phase of the emulsion, which "addition amount" is determined under standard conditions (20° C., standard pressure) by dissolving the maximal amount of active ingredient in the separate oil and aqueous phases (maintaining the other dissolution conditions identical) corresponding to the proportions in the dispersion (saturation concentrations).

Typical active ingredient concentrations in the dispersion are 0.01 wt. % to 30 wt. %, preferably 0.1 wt. % to 10 wt. %, particularly preferred 1 wt. % to 5 wt. %, based on the total amount of the dispersion.

Drugs of special interest—apart from amphotericin B—are vancomycin and vecuronium. Furthermore poorly soluble drugs can be taken from the groups of the prostaglandines, e.g. prostaglandine $E_2$, prostaglandine $F_{2á}$ and prostaglandine $E_1$, proteinase inhibitors, e.g. indinavire, nelfinavire, ritonavire, saquinavir, cytotoxics, e.g. paclitaxel, doxorubicine, daunorubicine, epirubicine, idarubicine, zorubicine, mitoxantrone, amsacrine, vinblastine, vincristine, vindesine, dactiomycine, bleomycine, metallocenes, e.g. titanium metallocene dichloride, and lipid-drug conjugates, e.g. diminazene stearate and diminazene oleate, and generally poorly insoluble anti-infectives such as griseofulvine, ketoconazole, fluconazole, itraconazole, clindamycine, especially antiparasitic drugs, e.g chloroquine, mefloquine, primaquine, pentamidine, metronidazole, nimorazole, tinidazole, atovaquone, buparvaquone, nifurtimoxe and anti-inflammatory drugs, e.g. cyclosporine, methotrexate, azathioprine.

Dispersions with anti-inflammatory drugs can be applied topically, orally and parenterally. In case of topical administration to the skin, the drug can penetrate into the tissue underneath to treat inflammatory processes. In case of topical application to mucosal surfaces such as the eye, diseases like the dry eye syndrome can be treated which are caused by an underlying inflammatory process. Topical administration to mucosal surfaces in the vagina is also favorable, e.g. especially for anti-infectives. The dispersions spread well over the membrane surface giving an equal distribution of the drug. Especially in case the dispersions contain oil droplets and additionally ultrafine drug crystals, these ultrafine crystals can adhere to the vaginal membrane and slowly dissolve providing prolonged drug action (depot). For administration to the eye it is favorable to use dispersions which are positively charged. The interaction of positively charged particles with negatively charged cell membranes will prolong the retention time.

Oral administration of the invented dispersions is favorable to increase the bioavailability of poorly soluble drugs being not sufficiently orally available, examples are paclitaxel and amphotericin B. Instead of applying an aqueous dispersion, the dispersions can also be transferred to a dry form by spray-drying or lyophilisation.

Parenteral, especially intravenous administration of drug-loaded dispersions can reduce the side effects, e.g. for doxorubicine, daunorubicine and Amphotericin B. Intravenously administered dispersions can be directed to desired target sites such as the brain and the bone marrow by modification of the surface with apolipoproteins. This is of special interest of drugs which have no or only limited accessibility to the brain and the bone marrow. Classical examples are cytotoxics such as doxorubicine. Targeting of cytotoxic dispersions to the brain will allow to treat brain tumors which by now could only be treated by irradiation or locally, e.g. by implanting therapeutic devices or drug-loaded implants. Dispersions with anti-infectives possessing poor blood-brain-barrier permeability could be used to deliver these anti-infectives across the blood-brain-barrier to treat parasites persisting in the brain.

The organ distribution of intravenously injected carriers is affected by the physico-chemical properties such as particle size, particle charge and surface hydrophobicity. For example, negatively charged particles are taken up much faster by the macrophages of the liver than uncharged particles (Wilkens, D, J. and Myers, P. A., Studies on the relationship between the electrophoretic properties of colloids and their blood clearance and organ distribution in the rat. Brit. J. Exp. Path. 47, 568-576, 1966). To modulate the in vivo organ distribution the charge of the invented dispersions can therefore be changed, again especially positively charged dispersions are favorable. At the injection site the positively charged dispersions can stick to negatively charged cell surfaces. After intravenous injection the negatively charged dispersion particles will interact with negatively charged proteins, especially with albumin being the most dominant protein in the blood. Albumin is known as dysopsonine, therefore adsorption onto the droplet surface and formation of an albumin adsorption layer can prolong the retention time of the invented dispersions in the blood (i.e. reduced uptake by the macrophages of the liver).

Positively charged dispersions according to the invention can be produced by using positively charged surfactants or using positively charged surfactants in mixture with uncharged stabilizers (e.g. poloxamers) and/or negatively charged surfactants (e.g. lecithin). Positively charged dispersions according to the invention possess a positive zeta potential. The zeta potential of the dispersion particles is determined by electrophoretic measurement in distilled water (conductivity adjusted to 50 μS/cm by addition of sodium chloride) or by measuring the particles in their original dispersion medium (i.e. outer phase of the dispersion). Examples for positively charged surfactants and stabilizers are stearylamine, cetylpyridiniumchloride (CPC), positively charged lipids, e.g. N-[1-(2,3-dioleyloxy)propyl]-N,N, N-tromethylammoniumchloride (DOTMA), didodecyldimethylammoniumbromide (DDAB), 2,3-dioleyloxy-N-[2(spermidincarboxamid)ethyl]-N,N-dimethyl-1-propylammoniumtrifluoroacetate (DOSPA), 3â-[N-(N',N'-dimethylaminoethan)carbamoyl]-cholesterol (DC-Chol).

Preparation of positively charged dispersions can be performed by using the positively charged surfactant or the surfactant mixture in the production process (de novo production). Alternatively, the positively charged surfactant can be added to a prepared negatively charged dispersion. It needs to be added in such a quantity that charge reversal from negative to positive occurs.

Details of the production process: The mixture of lipid, drug, water and surfactant or other stabilizers needs to undergo a higher energetic dispersion process. In case when using blends of oils and solid fats, it might be sensible to dissolve a solid fat in the oil at elevated temperature before preparing the mixture. Preferred method for producing the invented dispersion is high pressure homogenization, e.g. using piston-gap homogenizers or jet stream homogenizers. In case water is the outer phase of the dispersion, high pressure homogenization is performed between 0° C. and 100° C. Most efficient dispersion in combination with fast dissolution of the poorly soluble drug is achieved when homogenizing well above room temperature, e. i. between 35° C. and 100° C. Optimum homogenization temperatures considering simultaneously the chemical stability of the drug were found to be between 45° C. and 65° C. In case of highly temperature sensitive drugs, homogenization should be performed close to the freezing point of water (e.g. approx. 4° C.).

In case liquids other than water are forming the outer phase of the dispersion possessing a boiling point above water, homogenization can also be performed at higher temperatures or below 0° C. (e.g. PEG 600).

In case of lipid blends, blending the oil bulk with the solid lipid bulk might lead to a solid bulk blend—despite the particles in the produced dispersion being liquid (Thomson effect). In such a case homogenization should be performed at temperatures above the melting point of the bulk blend. The same is valid when using a solid lipid only to produce the dispersion according to the invention. The homogenization pressure applied can range from 10 bar to 11,000 bar. In case dispersions are produced at 11,000 bar, the dispersions are sterile because the high pressure disrupts bacteria and viruses. If sterility by homogenization is not desired, preferred production pressures are between 200 bar and approx. 4000 bar. High pressure production lines running in industry work typically between 200 bar and 700 bar, production at these pressures would not require to buy new machines. However, production at lower pressures requires a higher number of cycles. In case a higher number of cycles should be avoided (e.g. due to chemical stability aspects of the drug), a higher pressure should be applied ranging from 700 bar to 4000 bar. For 700-1500 bar homogenizers from APV Gaulin (Lübeck, Germany) can be used, 700-2000 bar can be run with machines from Niro Soavi (Lübeck, Germany), special homogenizers from the company Stansted allow pressures up to 4000 bar (Stansted, UK).

To produce the dispersion all homogenization equipment can be used providing a sufficiently high power density, that means typically above $10^4$ W/m$^3$. In some homogenizing machines the power density (dissipated energy per dispersion volume unit) cannot be calculated because the exact size of the dispersion volume is not known (e.g. microfluidizer). In such cases the suitability of the machine for producing the invented dispersion can only be determined by an empirical trial. Examples for homogenizers of the piston-gap type are the machines by the companies APV Gaulin, Niro Soavi, Stansted and also the French Press, an example for a jet stream homogenizer is the microfluidizer (Microfluidics, Inc., USA).

The invention is further illustrated by way of the following examples, however, without limiting it thereto.

EXAMPLES

Example 1

8 mg Amphotericin B were triturated with 40 g Lipofundin N 20% (0.2 mg Amphotericin B/ml emulsion) and the dispersion obtained was stirred with an Ultra-Turrax stirrer for 5 minutes at 8000 rpm. The dispersion was then subjected to high pressure homogenization with a Micron LAB 40 at 1,500 bar with 20 cycles. The particle size was determined using a laser diffractometer (Coulter LS 230, Coulter Electronics, USA). The diameter of 50% (D50%) of the volume distribution amounted to 0.164 µm, D90%, 0.340 µm, D95%, 0.387 µm, D99% 0.466 µm, and D100% 0.700 µm.

Example 2

An emulsion system with Amphotericin B was produced as in Example 1, the quantity of Amphotericin B incorporated however amounted to 40 mg (i.e. 1 mg/ml emulsion). The following diameters were measured: D50%, 0.160 µm, D90%, 0.362 µm, D95%, 0.406 µm, D99% 0.485 µm, and D100% 0.746 µm.

Example 3

An emulsion was produced analogous to that of Example 1, however the quantity Amphotericin B incorporated amounted to 80 mg (i.e. 2 mg/ml emulsion). The following diameters were measured: D50%, 0.194 µm, D90%, 0.381 µm, D95%, 0.423 µm, D99% 0.494 µm, and D100% 0.721 µm.

Example 4

40 mg Amphotericin B powder were triturated with 40 g oil (mixture 50:50 of LCT and MCT) and the suspension obtained was stirred with an Ultra-Turrax for 5 minutes as in Example 1. The suspension was then subjected to high pressure homogenization with a Micron LAB 40 high pressure homogenizer with 2 cycles at 150 bar, 2 cycles at 500 bar, and then 20 cycles at 1,500 bar. 8 g of the oily suspension obtained were then dispersed in 32 g water, which contained 1.2% lecithin. Dispersion was carried out with an Ultra-Turrax for 5 minutes at 8000 rpm. The dispersion obtained was then subjected to high pressure homogenization with the Micron LAB 40 at 500 bar with 10 cycles. The following diameters were measured: D50%, 0.869 µm, D90%, 2.151 µm, D95%, 2.697 µm, D99% 3.361 µm.

Example 5

An emulsion was produced, analogous to Example 4, however the production of the emulsion with high pressure homogenization was not carried out at room temperature, but in a temperature-controlled LAB 40 at 50° C. The following diameters were measured: D50%, 0.647 µm, D90%, 1.537 µm, D95%, 1.768 µm, D99% 2.152 µm, and D100% 3.310 µm.

Example 6

An Amphotericin B emulsion was produced by high pressure homogenization, analogous to Example 1 (0.2 mg Amphotericin B/ml emulsion), the high pressure homogenization of the emulsion took place at room temperature. The drug was triturated with a 1.2% aqueous Tween 80 solution, the suspension pre-homogenized and 80 mg of this suspension was mixed with 40 g Lipofundin N 20%. The following diameters were measured: D50% 0.142 µm, D90% 0.282 µm, D95% 0.331 µm, D99% 0.459 µm, and D100% 0.843 µm.

Example 7

An emulsion was produced, analogous to Example 6, however the Amphotericin B concentration amounted to 1 mg/ml emulsion. The following diameters were measured: D50% 0.245 µm, D90% 0.390 µm, D95% 0.426 µm, D99% 0.489 µm, and D100% 0.700 µm.

Example 8

An emulsion was produced, analogous to Example 6, however the Amphotericin B concentration amounted to 2 mg/ml emulsion. The following diameters were measured: D50% 0.237 µm, D90% 0.389 µm, D95% 0.426 µm, D99% 0.491 µm, and D100% 0.701 µm.

Example 9

An emulsion was produced, analogous to Example 6, however the high pressure homogenization of the emulsion took place at 60° C. The following diameters were measured: D50% 0.197 µm, D90% 0.388 µm, D95% 0.436 µm, D99% 0.532 µm, and D100% 0.953 µm.

Example 10

An emulsion was produced, analogous to Example 7, however the homogenization pressure amounted to 500 bar instead of 1500 bar. The following diameters were measured: D50% 0.263 µm, D90% 0.401 µm, D95% 0.435 µm, D99% 0.493 µm, and D100% 0.657 µm.

Example 11

Figure 1A:
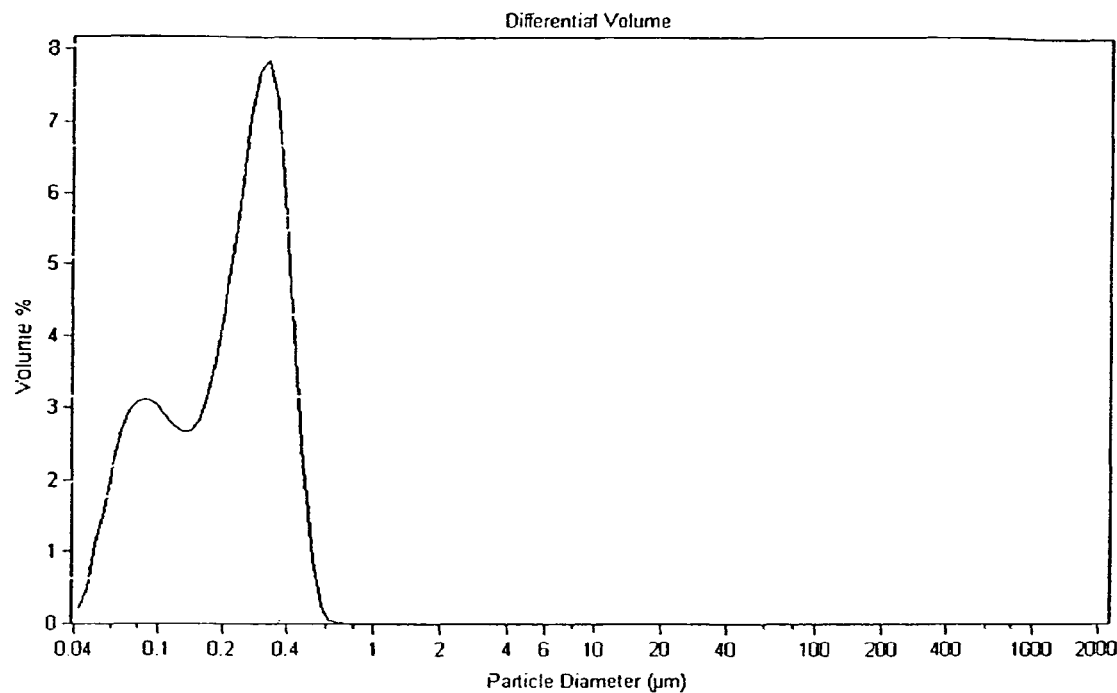
FIGS. 1A and 1B.
Figure 1B:
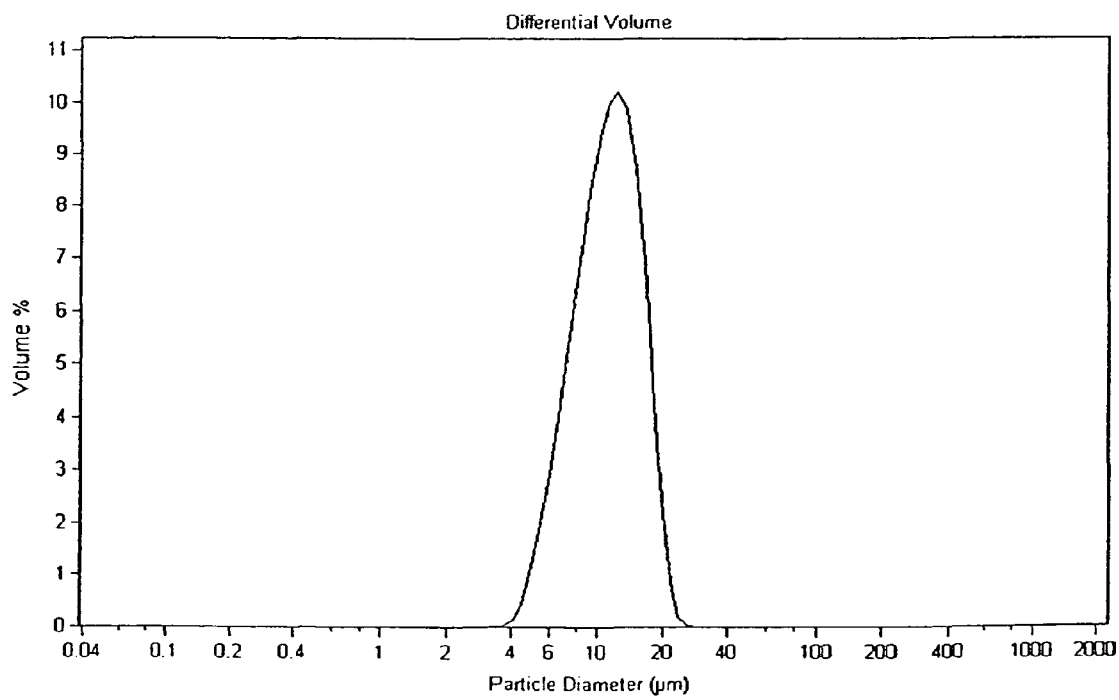

The particle size distribution of the Amphotericin B powder was analyzed with laser diffractometry and light microscopy. FIG. 1 (top) shows the particle size distribution curve of the Amphotericin B powder following dispersion in water, determined by laser diffractometry and the particle size distribution after incorporation into the emulsion system according to the invention from Example 2 (FIG. 1, bottom). In the emulsion system no Amphotericin B crystals remain detectable, Amphotericin B has been incorporated into the emulsion system.

Example 12

The Amphotericin B emulsion was examined in comparison with Amphotericin B crystals dispersed in water, using light microscopy. FIG. 2 shows the light microscopic photograph of the Amphotericin B powder in the polarized light, because of the anisotropy of the crystals they appear light. FIG. 3 shows the light-microscopic photograph in the polarized light following incorporation of Amphotericin B into the emulsion system (Example 1), anisotropic structures are no longer detectable, the whole picture is almost black. For the light microscopy, the emulsion system was applied to the slide undiluted.

Example 13

Buparvaquone was incorporated into an emulsion system analogously to the Amphotericin B as in Example 6. The following diameters were measured: D50% 0.399 μm, D90% 0.527 μm, D95% 0.564 μm, D99% 0.635 μm, and D100% 0.843 μm.

Example 14

Atovaquone was incorporated, analogously to Example 1, instead of Amphotericin B into an emulsion system. The following diameters were measured: D50% 0.297 μm, D90% 0.437 μm, D95% 0.475 μm, D99% 0.540 μm, and D100% 0.744 μm.

Example 15

An emulsion was produced analogously to Example 1, however the quantity of Amphotericin incorporated amounted to 5 mg/ml emulsion. The solubility in the dispersion for Amphotericin was exceeded, drug crystals were present besides oil drops (heterogeneous dispersion).

Example 16

An Amphotericin B emulsion was produced by adding 40 mg Amphotericin B to 40 mL of Lipofundin N 20% (i.e. Amphotericin B 1 mg/ml emulsion). The mixture was homogenized at 45° C., 1500 bar for 10 cycles. Sterilization was performed by autoclaving at 121° C. for 15 minutes according to the German pharmacopoeia The PCS diameter before autoclaving was 203 nm, the polydispersity index 0.102, after autoclaving the diameter was 208 nm, the polydispersity index 0.137.

Example 17

100 mg Amphotericin B powder were dispersed in 900 mg sterile water, pre-homogenized and dispersed in 20 g of MCT oil using pistil and mortar under the addition of 1.2% lecithin. The oil was dispersed in 80 g water and this mixture homogenized in a microfluidizer type Microfluidix M110y (i.e. Amphotericin B 1 mg/ml emulsion). Homogenization was performed at 1000 bar for 10 minutes. PCS diameter before autoclaving was 192 nm, the polydispersity index 0.113, after sterilization the diameter was 196 nm, the polydispersity index 0.109.

Example 18

The Amphotericin B emulsion from example 17 was analyzed undiluted for larger particles and potential Amphotericin B crystals by taking light microscopy graphs of the undiluted emulsion. FIG. 1 shows only a few larger droplets, no Amphotericin B crystals were detectable.

Example 19

Emulsions were produced as described in example 16, however 15 homogenization cycles were applied. Two dispersions were produced containing 1 mg/mL Amphotericin B and 5 mg/mL Amphotericin B. The emulsions were analyzed by taking light microscopy graphs. Light microscopy of the dispersion with 1 mg/ml shows an emulsion system with no detectable Amphotericin B particles (FIG. 5), in the dispersion with 5 mg/mL Amphotericin B besides the emulsion droplets very tiny Amphotericin B crystals are detectable (FIG. 6).

Example 20

An Amphotericin B emulsion was produced as described in example 16, production temperature was 65° C., 20 cycles were applied. The mean PCS diameter was 255 nm, the polydispersity index 0.098. Laser diffractometer analysis was performed using a Coulter LS 230 (Coulter Electronics, USA). The diameter 50% was 0.247 μm, the diameter 90% 0.410 μm, the diameter 99% 0.566 μm and the diameter 100% 0.938 μm. Amphotericin B content was 1 mg/ml, sterilization was performed by autoclaving at 121° C. for 15 minutes. Drug content was analyzed by HPLC, in two samples 93.8% and 91.0% were recovered, respectively.

Example 21

100 mg cyclosporine were mixed with 40 g of Lipofundin N 20%, homogenization was performed at temperature of 25° C. applying 20 cycles at 1500 bar. The mean PCS diameter was 234 nm, the polydispersity index 0.099. The laser diffractometer diameter 50% was 0.218 μm, the diameter 90% 0.381 μm and the diameter 100% 0.721 μm. In light microscopy no cyclosporine particles were detectable (polarized light, dark field). The zeta potential of the emulsion was determined in distilled water with conductivity adjusted to 50 μS/cm by addition of sodium chloride. Field strength was 20 V/cm, conversion of electrophoretic mobility to the zeta potential was performed using the Helmholtz-Smoluchowski equation. The zeta potential was −51 mV.

Example 22

A cyclosporine emulsion was produced as described in example 21, but 0.5% cetylpyridinium chloride (CPC) were added in the production process. The emulsion was positively charged, the zeta potential was +32 mV.

Example 23

A cyclosporine emulsion was produced as described in example 21 but under addition of 1.0% stearylamine. The PCS diameter was 247 nm, the polydispersity index 0.088. The laser diffractometer diameter 50% was 0.229 μm, the diameter 90% 0.389 μm and the diameter 100% 0.721 μm. The zeta potential was +24 mV.

Example 24

A cyclosporine emulsion was produced de novo. The composition was 0.1% cyclosporine, 0.5% poloxamer 188, 0.5% egg lecithin lipoid E80, 0.15% stearylamine, 10% miglyol 812 and 2.25% glycerol for isotonicity and water up to 100%. The lecithin was dispersed in the oil phase, a pre-emulsion was prepared with all the other ingredients by high speed stirring, cyclosporine powder was added in the last step. This mixture was homogenized at 45° C. applying 20 cycles and 1500 bar. The PCS diameter was 226 nm, the polydispersity index 0.111. The laser diffractometer diameter 50% was 0.200 μm, the diameter 90% 0.406 μm and the diameter 100% 1.154 μm The emulsion was positively charged, the zeta potential was +31 mV.

Example 25

An O/W dispersion was produced being composed of 10 g water phase containing 25 mg Amphotericin, 0.5 g Span 85, 0.25 g Tween 80 and Miglyol 812 added to 50 g. 1.0 ml of Amphotericin suspension (2.5% Amphotericin/ml) stabilized with 2.4% lecithin lipoid E 80 was mixed with distilled water to yield 10 g, Tween 80 was added to the water phase, Span 85 to the oil phase. The water was dispersed in the oil by high speed stirring. The obtained pre-emulsion was homogenized at 90° C. applying 1500 bar and 20 homogenization cycles. Size analysis was performed by laser diffractometry (Mastersizer E, Malvern Instruments, UK). The diameter 50% was 2.25 µm, the diameter 90% 4.21 µm.

While the claimed invention has been described in detail and with reference to specific embodiments thereof, it will be apparent to one of ordinary skill in the art that various changes and modifications can be made to the claimed invention without departing from the spirit and scope thereof.

I claim:

1. A supersaturated dispersion which comprises:
   an oily phase;
   an aqueous phase, in the form of an oil-in-water emulsion or a water-in-oil emulsion; and
   at least one active ingredient that is only slightly or with difficulty soluble in the oily phase and the aqueous phase, wherein the dispersion is free from toxicologically dangerous organic solvents and the dispersion is supersaturated containing the active ingredient dissolved in a quantity that is at least 5 times greater than the quantity which results additively from its maximum solubility in the oily and the aqueous phase of the emulsion, said dispersion obtained by combining;
   the aqueous phase,
   the oily phase, which oily phase is not or only partially miscible with the aqueous phase,
   the surfactant or stabilizer, and
   a solid phase, which comprises the one active ingredient, to form a pre-dispersion, wherein the active ingredient is suspended in at least a portion of the aqueous phase before contacting the active ingredient with the oily phase,
   which pre-dispersion of liquid and solid phases is subjected to a high-energy homogenization process wherein no toxicologically dangerous solvents are used, and wherein at least one of
   the at least one active ingredient is incorporated as solid particles into the liquid phases of the dispersion without previously being dissolved,
   the at least one active ingredient is pulverized to form particles, the particles of active ingredient are triturated or mixed with an oil-in-water emulsion or a water-in-oil emulsion to form the pre-dispersion, or
   the at least one active ingredient is pulverized to form particles, the particles of active ingredient are added to a surfactant solution, said surfactant solution is homogenized and mixed with an oil-in-water emulsion or a water-in-oil emulsion to form the pre-dispersion.

2. Dispersion according to claim 1, wherein the active ingredient, in addition to the dissolved state, is partially present in highly dispersed solid crystalline form, resulting in a dispersion with a heterogeneously dispersed phase of oil drops and active ingredient crystals.

3. Dispersion according to claim 2, wherein at least 90% of the active ingredient crystals present are smaller than 5 µm, volume distribution determined by laser diffractometry.

4. Dispersion according to claim 2, wherein at least 95% of the active ingredient crystals present are smaller than 5 µm, volume distribution determined by laser diffractometry.

5. Dispersion according to claim 2, wherein about 100% of the active ingredient crystals present are smaller than 5 µm, volume distribution determined by laser diffractometry.

6. Dispersion according to claim 2, wherein at least 90% of the active ingredient crystals present are smaller than 3 µm, volume distribution determined by laser diffractometry.

7. Dispersion according to claim 2, wherein at least 95% of the active ingredient crystals present are smaller than 3 µm, volume distribution determined by laser diffractometry.

8. Dispersion according to claim 2, wherein about 100% of the active ingredient crystals present are smaller than 3 µm, volume distribution determined by laser diffractometry.

9. Dispersion according to claim 2, wherein at least 90% of the active ingredient crystals present are smaller than 1 µm, volume distribution determined by laser diffractometry.

10. Dispersion according to claim 2, wherein at least 95% of the active ingredient crystals present are smaller than 1 µm, volume distribution determined by laser diffractometry.

11. Dispersion according to claim 2, wherein about 99% of the active ingredient crystals present are smaller than 1 µm, volume distribution determined by laser diffractometry.

12. Dispersion according to claim 1, wherein the dispersion comprises an oil-in-water emulsion and contains about 5 to about 99.5 wt. % of aqueous phase, based on the total weight of the dispersion.

13. Dispersion according to claim 1, wherein the dispersion comprises an oil-in-water emulsion and contains about 10 to about 95 wt. % of aqueous phase, based on the total weight of the dispersion.

14. Dispersion according to claim 1, wherein the dispersion comprises an oil-in-water emulsion and contains about 60 to about 95 wt. % of aqueous phase, based on the total weight of the dispersion.

15. Dispersion according to claim 1, wherein the dispersion comprises an oil-in-water emulsion and contains about 70 to about 95 wt. % of aqueous phase, based on the total weight of the dispersion.

16. Dispersion according to claim 1, wherein the dispersion contains at least one selected from the group consisting of emulsifiers and stabilizers.

17. Dispersion according to claim 16, wherein the dispersion contains less than 15 wt. % of emulsifiers and/or stabilizers, based on the total weight of the dispersion.

18. Dispersion according to claim 16, wherein the dispersion contains less than 10 wt. % of emulsifiers and/or stabilizers, based on the total weight of the dispersion.

19. Dispersion according to claim 16, wherein the dispersion contains less than 2 wt. % of emulsifiers and/or stabilizers, based on the total weight of the dispersion.

20. Dispersion according to claim 16, wherein the dispersion contains from about 0.6 to about 1.2 wt. % of emulsifiers and/or stabilizers, based on the total weight of the dispersion.

21. Dispersion according to claim 1, wherein the dispersion comprises at least one emulsifier selected from the group consisting of egg lecithin, soya lecithin, phospholipids of egg or soya, sorbitan esters, sorbitane trioleate, polyethylene glycol sorbitan esters, polyoxyethylene sorbitane monooleate, sodium glycocholate, sodium lauryl sulphate, and mixtures thereof.

22. Dispersion according to claim 1, wherein the dispersion comprises at least one stabilizer selected from the group consisting of block co-polymers, poloxamers, Poloxamer 188 and 407, poloxamines, Poloxamine 908, polyvinyl pyrrolidone, polyvinyl alcohol, gelatine, polysaccharide, hyaluronic acid, chitosan, derivatives of chitosan, polyacryl acid, derivatives of polyacryl acid, polycarbophil, cellulose derivatives, methyl cellulose, hydroxypropyl cellulose, carboxymethyl cellulose, sugar esters, saccharose monostearate, sodium citrate individually, and mixtures thereof.

23. Dispersion according to claim 1, wherein the dispersion comprises an oil-in-water emulsion and the oil phase used for the preparation of the dispersion comprises lipids which are solid at room temperature.

24. Dispersion according to claim 1, wherein the dispersion comprises an oil-in-water emulsion and the oil phase used for the preparation of the dispersion comprises lipids which are liquid at room temperature.

25. Dispersion according to claim 1, wherein the dispersion comprises an oil-in-water emulsion and the oil phase used for the preparation of the dispersion comprises a mixture of one or more lipids which are liquid at room temperature with one or more lipids which are solid at room temperature.

26. Dispersion according to claim 25, wherein the mixture of liquid lipid:solid lipid varies from about 99:1 to about 1:99 parts by weight.

27. Dispersion according to claim 26, wherein proportion of liquid lipid in mixture of lipids is at least 10 parts by weight.

28. Dispersion according to claim 26, wherein proportion of liquid lipid in mixture of lipids is at least 30 parts by weight.

29. Dispersion according to claim 26, wherein proportion of liquid lipid in mixture of lipids is at least 50 parts by weight.

30. Dispersion according to claim 1, wherein the oil phase comprises at least one individual lipid or mixtures thereof selected from the group consisting of natural and synthetic triglycerides, natural and synthetic monoglycerides, natural and synthetic diglycerides, self-emulsifying modified lipids, natural and synthetic waxes, fatty alcohols, esters of fatty alcohols, ethers of fatty alcohols, hard wax, Imwitor 900, glycerol trilaurate, glycerol myristate, glycerol palmitate glycerol stearate, glycerol behenat, waxes, cetyl palmitate, carnauba wax, white wax, hydrocarbons, and hard paraffin.

31. Dispersion according to claim 1, wherein the an oil phase comprises at least one selected from the group consisting of soya oil, safflower oil, long-chain triglycerides, medium-chain triglycerides, miglyols, fish oils, oils with an increased constituent of unsaturated fatty acids, and acetylated partial glycerides.

32. Dispersion according to claim 1, wherein the aqueous phase comprises water or mixtures of water with water-miscible organic liquids.

33. Dispersion according to claim 1, wherein the aqueous phase comprises water and at least one liquid polyethylene glycol.

34. Dispersion according to claim 1, wherein the aqueous phase contains at least one additive selected from the group consisting of electrolytes, non-electrolytes, glycerol, glucose, mannitol, xylite, gel forming agents, cellulose, and cellulose derivatives.

35. Dispersion according to claim 1, wherein the active ingredient is selected from the group consisting of medical drugs for treatment of human or animal bodies.

36. Dispersion according to claim 1, wherein the dispersion contains one or more active ingredients selected from the group consisting of anaesthetics, antibiotics, antimycotics, antiinfectives, corticoids, hormones, antiestrogens antiseptics, vasoactivating agents, glauco agents, beta blocker, cholinergics, sympathomimetics, carboanhydrase inhibitors, mydriatics, virustatics, agents for tumor therapy, antiallergics, vitamins, antiinflammytory drugs, immuno-supressives, ciclosporine, and any combination thereof.

37. Dispersion according to claim 1, wherein the dispersion is positively charged.

38. Dispersion according to claim 1, wherein the dispersion comprises at least one positively charged stabilizer.

39. Dispersion according to claim 1, wherein the dispersion comprises at least on positively charged stabilizer selected from the group consisting of stearylamine, positively charged phospholipids, and positively charged lipids.

40. Dispersion according to claim 1, wherein the dispersion comprises an oil-in-water emulsion adapted for intravenous injection, and wherein the dispersion comprises at least on positively charged stabilizer.

41. Dispersion according to claim 40, wherein the dispersion further includes at least one lecithines or nonionic stabilizers.

42. Dispersion according to claim 40, wherein the dispersion further comprises at least one poloxamer polymer.

43. Dispersion according to claim 1, wherein the active ingredient comprises ciclosporine.

44. Dispersion according to claim 1, wherein the active ingredient comprises at least one selected from the group consisting of anti-mycotics, Amphotericin B, anti-infectives, Buparvaquone, Atovaquone, immuno-suppressives, Cyclosporin A, natural and synthetic derivatives of Cyclosporin A, tumor therapy drugs, Paclitaxel, and Taxotere.

45. Dispersion according to claim 1, wherein the active ingredient has a solubility of less than 1 part per 100 parts in the aqueous phase.

46. Dispersion according to claim 1, wherein the active ingredient has a solubility of less than 1 part per 1000 parts in the aqueous phase.

47. Dispersion according to claim 1, wherein the active ingredient has a solubility of less than 1 part per 10,000 parts in the aqueous phase.

48. Dispersion according to claim 1, wherein the active ingredient has a solubility of less than 1 part per 100 parts in the oily phase.

49. Dispersion according to claim 1, wherein the active ingredient has a solubility of less than 1 part per 1000 parts in the oily phase.

50. Dispersion according to claim 1, wherein the active ingredient has a solubility of less than 1 part per 10,000 parts in the oily phase.

51. Dispersion according to claim 1, wherein the size of water phase and oily phase droplets is less than about 10 µm.

52. Dispersion according to claim 1, wherein the size of water phase and oily phase droplets is less than about 5 µm.

53. Dispersion according to claim 1, wherein the size of water phase and oily phase droplets is less than about 1 µm.

54. Dispersion according to claim 1, wherein a pH of the dispersion is between 4 and 8.

55. Dispersion according to claim 1, wherein a pH of the dispersion is between 5 and 7.5.

56. Dispersion according to claim 1, wherein a pH of the dispersion is between 6 and 7.5.

57. Dispersion according to claim 1, wherein the active ingredient is present in an amount of from about 0.01 to about 30 wt. %, based on the total weight of the dispersion.

58. Dispersion according to claim 1, wherein the active ingredient is present in an amount of from about 0.1 to about 10 wt. %, based on the total weight of the dispersion.

59. Dispersion according to claim 1, wherein the active ingredient is present in an amount of from about 1 to about 5 wt. %, based on the total weight of the dispersion.

60. A medicament comprising the dispersion according to claim 1.

61. A medicament for treatment of mycoses, inflammations, allergic diseases, tumor diseases, cardiovascular diseases, viral and other infections, or for conducting anaesthetic treatment comprising a dispersion according to claim 1.

62. A medicament which can be administered intravenously, intra- and subcutaneously, intramuscularly, intra-articularly or intraperitoneally comprising a dispersion according to claim 1.

63. A medicament which has a prolonged residence time in the blood, compared to negatively charged dispersions, comprising a dispersion according to claim 1.

64. Supersaturated dispersions in form of an oil-in-water emulsion comprising:
   an oil phase;
   a water phase;
   one or more surfactants or stabilizers; and
   one or more drugs being only slightly or poorly soluble in the water and in the oil, the dispersions are supersaturated and contain an incorporated amount of the drug in dispersion that is at least 5 times higher than the additive solubility calculated from the drug solubility in the oil and water phases of the dispersion, and the dispersions are organic solvent-free, said dispersion obtained by combining;
   the aqueous phase,
   the oily phase, which oily phase is not or only partially miscible with the aqueous phase,
   the surfactant or stabilizer, and
   a solid phase, which comprises the one or more drugs, to form a pre-dispersion, wherein the active ingredient is suspended in at least a portion of the aqueous phase before contacting the active ingredient with the oily phase,
   which pre-dispersion of liquid and solid phases is subjected to a high-energy homogenization process wherein no toxicologically dangerous solvents are used, and wherein at least one of the one or more drugs is incorporated as solid particles into the liquid phases of the dispersion without previously being dissolved,
   the one or more drugs is pulverized to form particles, the particles of drug are triturated or mixed with an oil-in-water emulsion or a water-in-oil emulsion to form the pre-dispersion, or
   the one or more drugs is pulverized to form particles, the particles of drug are added to a surfactant solution, said surfactant solution is homogenized and mixed with an oil-in-water emulsion or a water-in-oil emulsion to form the pre-dispersion.

65. Dispersions according to claim 64, wherein the concentration of surfactant, stabilizer or mixtures of surfactants and stabilizers is between 0.1% and 20% by weight.

66. Dispersion according to claim 1, wherein the active ingredient is dissolved in a quantity that is at least 10 times greater than the quantity which results additively from its maximum solubility in the oily and the aqueous phase of the emulsion.

67. Dispersions according to claim 64, wherein the active ingredient is dissolved in a quantity that is at least 10 times greater than the quantity which results additively from its maximum solubility in the oily and the aqueous phase of the emulsion.

68. A method for the production of a dispersion comprising:
   an oily phase;
   an aqueous phase, in the form of an oil-in-water emulsion or a water-in-oil emulsion; and
   at least one active ingredient that is only slightly or with difficulty soluble in the oily phase and the aqueous phase, wherein the dispersion is free from toxicologically dangerous organic solvents and the dispersion is supersaturated containing the active ingredient dissolved in a quantity that is at least 5 times greater than the quantity which results additively from its maximum solubility in the oily and the aqueous phase of the emulsion, the method comprising:
   suspending the active ingredient in at least a portion of the aqueous phase to form a suspension and mixing the suspension with said oily phase to form a mixture;
   subjecting the mixture of liquid and solid phases to a high-energy homogenization process with a homogenizer without using toxicologically dangerous organic solvents, wherein one of:
   (a) incorporating the active ingredient as a solid into the liquid phases of the dispersion without previously being dissolved,
   (b) pulverizing the active ingredient, triturating or mixing the pulverized active ingredient with an oil-in-water emulsion or a water-in-oil emulsion to form a pre-dispersion, and subjecting the pre-dispersion to the homogenization or high pressure homogenization process, or
   (c) pulverizing the active ingredient, dispersing the pulverized active ingredient in a surfactant solution, homogenizing the dispersion to form a homogenized dispersion, then mixing the homogenized dispersion with an oil-in-water emulsion or a water-in-oil emulsion to form a pre-dispersion, and subjecting the pre-dispersion to the homogenization or high pressure homogenization process.

* * * * *